US006581446B1

(12) United States Patent
Deneuville et al.

(10) Patent No.: US 6,581,446 B1
(45) Date of Patent: Jun. 24, 2003

(54) DETERMINATION OF ADHESION STRENGTH OF HVOF COATING BY SPHERICAL INDENTATION

(75) Inventors: Loic Deneuville, Houston, TX (US); Kenneth W. White, Kemah, TX (US); Krishnaswamy Ravi-Chandar, Austin, TX (US)

(73) Assignee: The University of Houston, Houston, TX (US)

( * ) Notice: Subject to any disclaimer, the term of this patent is extended or adjusted under 35 U.S.C. 154(b) by 0 days.

(21) Appl. No.: 09/958,618

(22) PCT Filed: Apr. 13, 2000

(86) PCT No.: PCT/US00/09940

§ 371 (c)(1),
(2), (4) Date: Oct. 11, 2001

(87) PCT Pub. No.: WO00/62038

PCT Pub. Date: Oct. 19, 2000

Related U.S. Application Data

(60) Provisional application No. 60/129,115, filed on Apr. 13, 1999.

(51) Int. Cl.[7] .................................................. G01N 3/48
(52) U.S. Cl. .......................................................... 73/81
(58) Field of Search ........................ 73/774, 762, 775, 73/790, 78, 81

(56) References Cited

U.S. PATENT DOCUMENTS

| 4,232,559 | A | | 11/1980 | Favre et al. |
|---|---|---|---|---|
| 4,263,811 | A | | 4/1981 | Shaw |
| 4,501,154 | A | | 2/1985 | Mori |
| 4,606,225 | A | | 8/1986 | Thomason et al. |
| 4,856,326 | A | * | 8/1989 | Tsukamoto ................ 73/150 A |
| 6,050,140 | A | | 4/2000 | Koch |
| 6,339,958 | B1 | * | 1/2002 | Tsui et al. ................. 73/290 R |
| 6,377,039 | B1 | * | 4/2002 | Goldfine et al. ............ 324/232 |
| 6,414,506 | B2 | * | 7/2002 | Akram et al. ................ 324/765 |

OTHER PUBLICATIONS

International Search Report for parent International Application, PCT/US00/09940, filed Apr. 13, 2000, earliest priority Apr. 13, 1999, entitled: Determination of Adhesion Strength of HVOF Coating By Spherical Indentation; Search Report Dated Jul. 31, 2000.

* cited by examiner

Primary Examiner—Max Noori
(74) Attorney, Agent, or Firm—Tim Headley; Gardere Wynne Sewell LLP

(57) ABSTRACT

A method for determining the adhesion strength of any HVOF-coating/substrate system. This method applies a spherical indentor to the coated part in a loading-unloading cycle. During the loading phase, the substrate deforms plastically. During the unloading phase, the elastic-plastic mismatch between coating and substrate material properties gives rise to a tensile stress normal to the interface. This leads to delamination for a sufficient indentation load. A hybrid numerical-experimental approach calculates the interfacial adhesion. The threshold load for delamination is found experimentally. A finite element model calculates the corresponding adhesion stress for delamination. This method enables the quantitative evaluation of the adhesion for any coating/substrate interface, regardless of bond strength.

7 Claims, 4 Drawing Sheets

Figure 3: Interfacial delamination nucleated by the tensile residual stress. The two arrows-heads show the contact region

DETERMINATION OF ADHESION STRENGTH OF HVOF COATING BY SPHERICAL INDENTATION

This application claims the benefit of Provisional application Ser. No. 60/129,115, filed Apr. 13, 1999.

TECHNICAL FIELD

This invention relates to the field of methods to determine adhesion properties of coatings, and, more particularly, to high adhesion strength HVOF (High Velocity Oxygen-Fuel) thermal sprayed coating.

BACKGROUND OF THE INVENTION

HVOF (High Velocity Oxygen Fuel) thermal sprayed coatings are often used to extend the service life of metal parts in harsh environment. In order to determine the viability of the coatings, it is necessary to determine the adhesive strength of the coating.

Therefore, a standard ASTM test (C633-79) has been developed for this purpose. In this standard test, termed Tensile Adhesion Test, a coated specimen is attached to a support fixture of a tensile testing machine by epoxy. A tensile force is then applied by the machine until the coating fails. The stress at failure is called the tensile adhesion strength or bond strength.

However, some of the HVOF coatings exhibit higher adhesion strength than epoxy glue such that the standard test leads to delamination of the epoxy instead of the coating.

Therefore, there is a need for a testing method that will determine the adhesion strength of coatings that exceed the capability of the ASTM C633-79 standard test.

SUMMARY OF THE INVENTION

The present invention is a technique that determines the adhesion strength of any HVOF-coating/substrate system by spherical indentation. We emphasize that while we have characterized HVOF coating/substrate system, and demonstrated the test for this case, the test method is generally applicable to all coatings, regardless of the method used to obtain the coating. The principle of the method is illustrated in FIG. 1. The coated part is subjected to a loading-unloading cycle using a spherical indentor. During the loading phase, the substrate deforms plastically and during the unloading phase, the elastic-plastic mismatch between coating and substrate material properties gives rise to a tensile stress normal to the interface that will lead to delamination for a sufficient indentation load. A hybrid numerical-experimental approach is used to calculate the interfacial adhesion; the threshold load for delamination is found experimentally and a finite element model is used to calculate the corresponding adhesion stress for delamination.

The present invention enables the quantitative evaluation of the adhesion for any coating/substrate interface, regardless of bond strength, while the prior art can only evaluate interface strengths of a bond strength less than that of the adhesive used for bonding the two ASTM samples.

LIST OF FIGURES

DETAILED DESCRIPTION OF THE PROCEDURE

Figure 2:
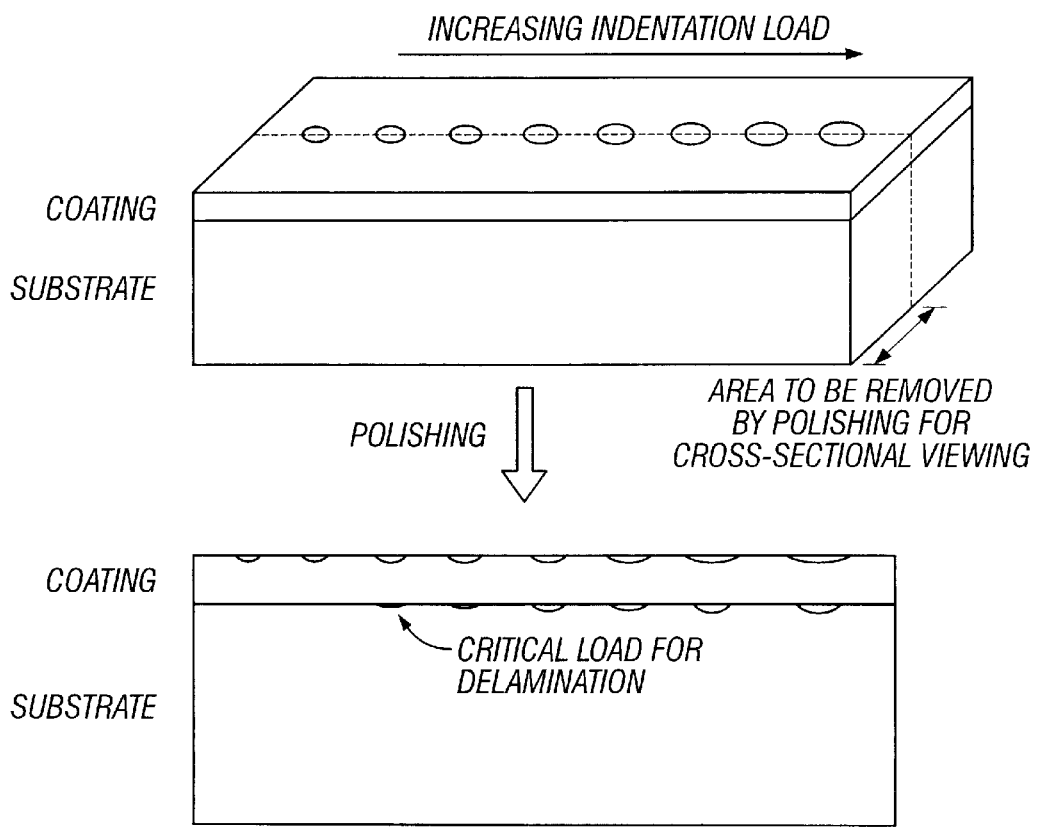
FIG. 2 is a schematic of the experimental procedure for the method.
Figure 3:
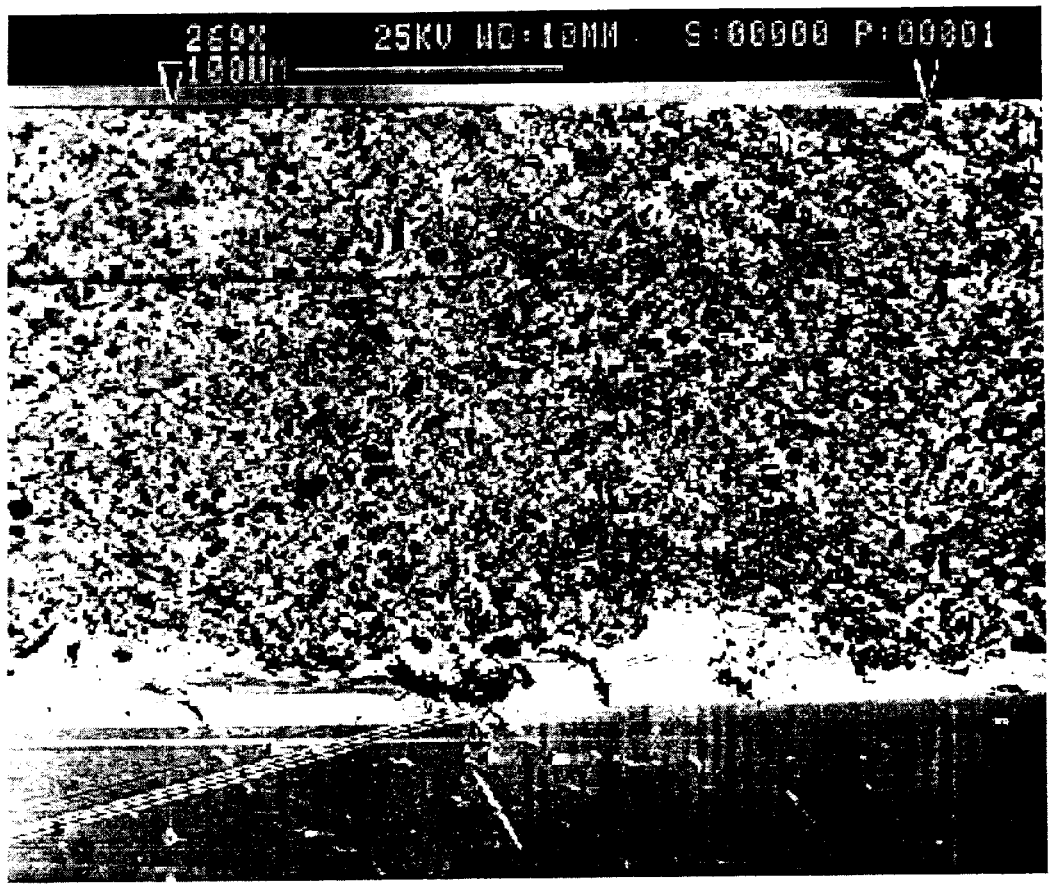
FIG. 3 is a micrograph of the sample at the critical load value.

The method that has been developed is a hybrid numerical-experimental method, as detailed here:

Experimental Determination of Critical Load (See Schematic of FIG. 2)

a) A row of indents are mechanically placed on the deposited coating, each with an increasing normal load.

b) The specimen is sectioned and polished carefully up to the fictive line corresponding to the centers of the indents.

c) Optical microscopy methods are used to identify the first appearance of coating delamination associated with one of the indents.

d) The corresponding peak indentation load is taken as the critical load. The critical load is the lowest indentation load at which an interfacial delamination is seen in the polished specimen.

Numerical Determination of Interfacial Adhesion Stress a) The spherical indentation experiment is modeled using finite element software. The geometry is represented through appropriate FEM meshing, including the spherical indenter in contact with a coated specimen.

b) The coating is represented as an upper layer of thickness corresponding to that of the real coating. The material properties of the coating and the substrate must be incorporated into the model.

c) The critical load found experimentally (see above) is now input to the finite element model. Displacement rates in this model faithfully simulate those from the experiment, as determined from the universal load frame.

d) The adhesion strength at the interface is taken as the normal tensile residual stress at the interface given by the model. We have determined that the contribution of shear stresses to delamination is negligible due to the topography typical of the grit-blasted substrate surface. It must be assured by microscopic observation that delamination occurred under tension and not by shear. This can be done by determining that the delamination was under the center of the indentor and not below the edge of the contact zone

EXAMPLES

The inventors used three different systems for the present invention. All the substrates were grit-blasted with aluminum oxide particles. The achieved roughness on the substrate after grit blasting was 300 Ra. Thermal sprayed coatings were then deposited using the HVOF technique. Alloy Carbide Co., Houston, Tex., performed all coating processes.

Two types of RAM (Rocket Applied Metallics) coatings were tested:

RAM31 whose composition is 80% $Cr_3C_2$/20% Ni-Cr with an average thickness of 250 microns;

RAM49 (Stellite®) whose composition is 67% Co, 28% Cr, 4% W and 1% C with an average thickness of 350 microns.

Both coatings were applied over a 17-4 PH stainless steel substrate. For RAM31, the coating was applied on two different 17-4PH stainless steel samples of different yield stresses. Mechanical properties of materials used for all combinations are summarized in the table1 below.

TABLE 1

| Material | Elastic modulus, E (GPa) | Poisson's ratio, □ | Yield stress, Y (GPa) | Hardening coefficient, □ |
|---|---|---|---|---|
| 17-4 PH; Sustrate 1 | 206.8 | 0.27 | 0.8 | 0 |
| 17-4 PH; Substrate 2 | 206.8 | 0.27 | 1.2 | 0 |
| RAM31 coating | 96 | 0.3 | 1.4 | 0.4 |
| RAM49 coating | 60 | 0.3 | 1 | 0.4 |
| WC-indentor | 614 | 0.22 | — | — |

Except for the Young modulus of the coatings, all elastic moduli and Poisson's ratio values were taken from the literature.

The elastic modulus of the coatings; yield stresses and hardening coefficients for all materials were determined by using an indentation technique. Using a universal test machine, indentations at different loads were performed with a tungsten carbide spherical indentor. The loading rate is low, followed by a rapid unloading rate. The residual impressions were measured optically using Nomarski illumination techniques.

The Young's modulus of the coatings were deduced from a plot of the indentation stress versus indentation strain.

For the plastic properties, the numerical model developed for the determination of the adhesion was used. A standard incremental J2 plasticity theory, with the Von Mises yield and the Prandtl-Reuss flow rule as implemented in ABAQUS was used to model plasticity. The tungsten carbide indentor was considered as remaining elastic during the indentation experiment and therefore described as perfectly elastic. Coating and substrate were considered as elastic-plastic material exhibiting a strain-hardening behavior.

Plastic properties of both coating and substrate were obtained by comparing experimental and numerically determined results, where different values for yield stress and hardening coefficient were input. When comparing experimental and numerical results at several loads, the combination of yield stress and hardening coefficient matching the experimental data was considered as being the material properties.

Once the model is totally defined in terms of mesh geometry and material properties, several rows of indents with increasing normal loads were performed on the different combinations of materials. Along each row, indentations were separated of 1 mm and the increment in load was 5 N. The rows were then polished carefully up to the row using a finishing abrasive paper grade of 800 in order not to damage the interface.

Once the material was sectioned through the center of the residual impressions, interface damage was observed with an optical microscope. Delamination is defined by the appearance of a crack of 25 microns or larger.

For each experiment, the finite element model was run with the indentation load corresponding to experimental delamination load. Adhesion strength of the coating/substrate interface was considered as being the simulated tensile residual stress normal to the interface along the centerline of the indentation.

Figure 4:
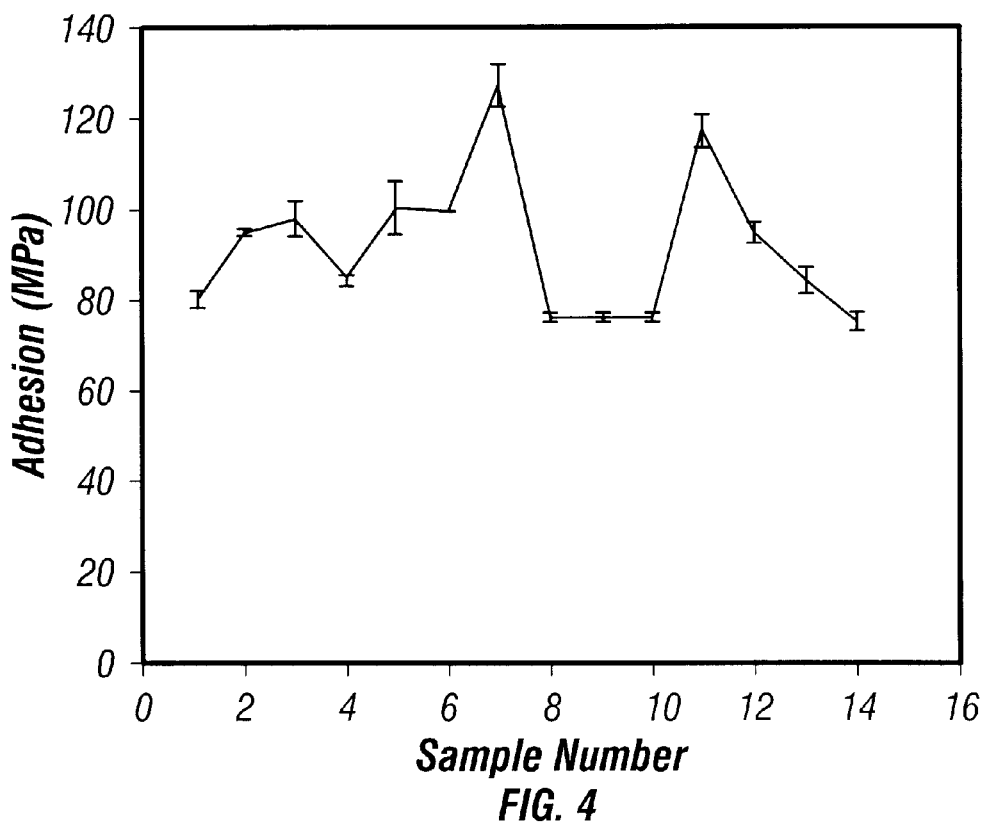
FIG. 4 is a graph showing the adhesion strength of RAM31 on 17-4 PH;substrate1.
Figure 5:
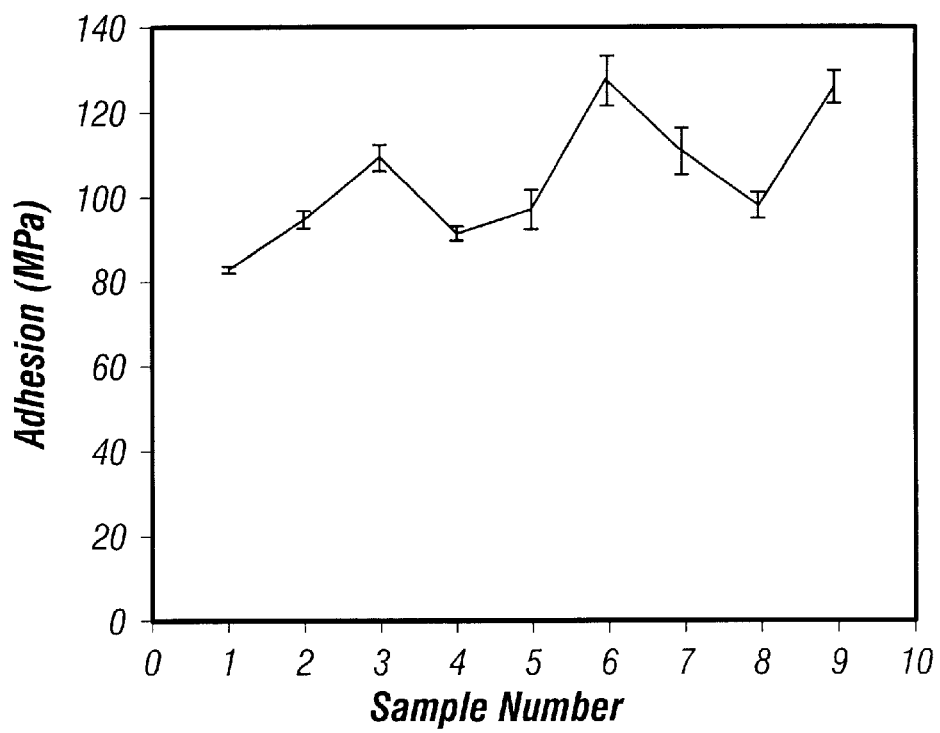
FIG. 5 is a graph showing the adhesion strength of RAM31 on 1 7-4PH;substrate2.
Figure 6:
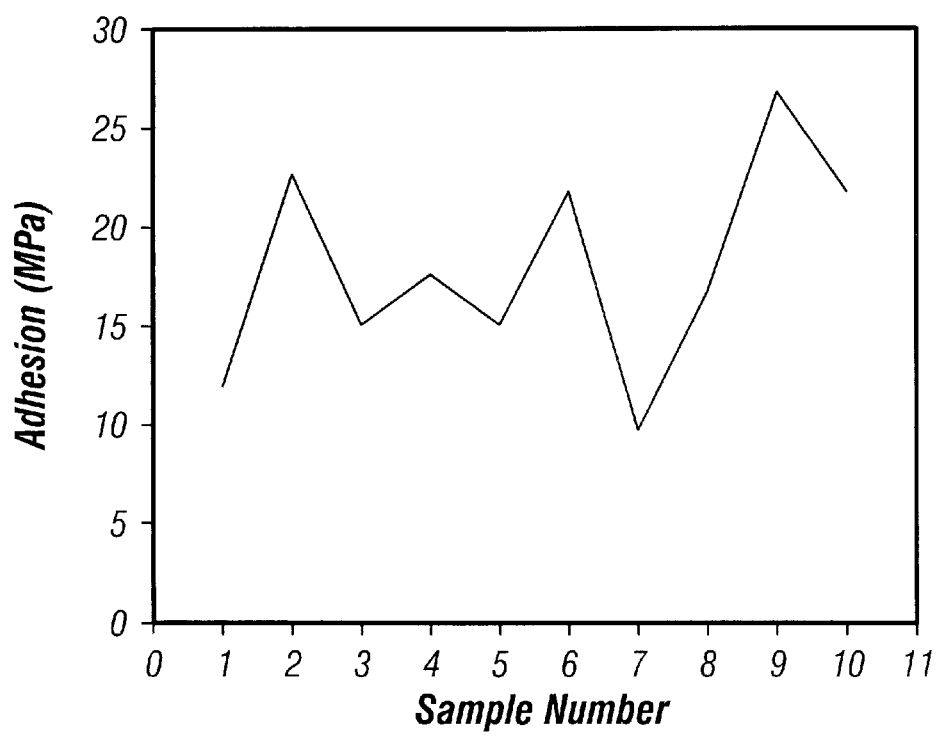
FIG. 6 is a graph showing the adhesion strength of RAM49 on 17-4PH;substrate2.

Adhesion results for the different combinations are in FIGS. 4, 5 and 6.

What is claimed is:

1. A method for determining a coating bond strength between a coating and a substrate, comprising the steps of:
   a. determining experimentally a critical load for delamination due to unloading of a spherical indentation;
   b. performing an FEM simulation of an indentation cycle at an experimental critical load; and
   c. deducing an adhesion stress at the interface from the FEM simulation.

2. The method of claim 1, further comprising the step of determining Young's modulus by spherical indentation using the Hertz theory for elastic contact.

3. The method of claim 2, further comprising the step of modeling the plastic properties of both the substrate and the coating by matching experimental and numerical results.

4. A method for determining interfacial adhesion between a first and a second thick film coating, comprising the steps of:
   a. determining experimentally a critical load for delamination due to unloading of a spherical indentation;
   b. performing an FEM simulation of an indentation cycle at an experimental critical load; and
   c. deducing an adhesion stress at the interface from the FEM simulation.

5. The method of claim 4, further comprising the step of determining Young's modulus by spherical indentation using the Hertz theory for elastic contact.

6. The method of claim 5, further comprising the step of modeling the plastic properties of both the first and the second thick film coatings by matching experimental and numerical results.

Figure 1:
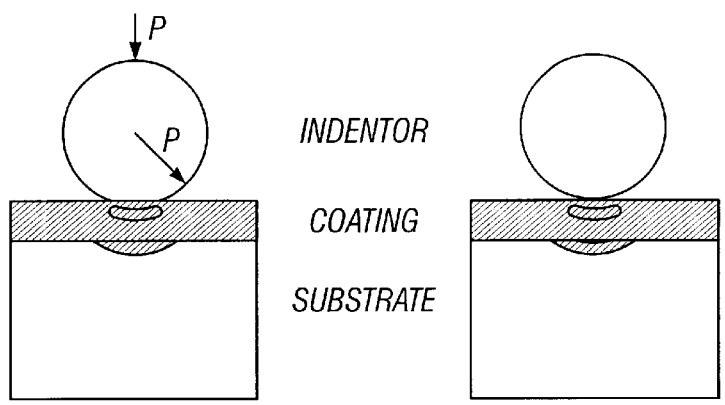
FIG. 1 is a schematic of the principle of the method.

7. The method of claim 6, wherein the thick film coatings are substrates.FIG. 1: principle of the method.

* * * * *